(12) United States Patent
Oku et al.

(10) Patent No.: US 8,574,212 B2
(45) Date of Patent: Nov. 5, 2013

(54) ABSORPTIVE ARTICLE INCLUDING WAISTLINE STRETCHING REGIONS

(75) Inventors: Tomomi Oku, Kagawa (JP); Satoru Sakaguchi, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 364 days.

(21) Appl. No.: 12/918,384

(22) PCT Filed: Feb. 17, 2009

(86) PCT No.: PCT/JP2009/052646
§ 371 (c)(1),
(2), (4) Date: Apr. 4, 2011

(87) PCT Pub. No.: WO2009/104581
PCT Pub. Date: Aug. 27, 2009

(65) Prior Publication Data
US 2011/0184368 A1    Jul. 28, 2011

(30) Foreign Application Priority Data

Feb. 19, 2008  (JP) .................................. 2008-037921

(51) Int. Cl.
*A61F 13/49* (2006.01)
*A61F 13/493* (2006.01)

(52) U.S. Cl.
USPC .............. 604/385.29; 604/385.24; 604/385.3; 604/394

(58) Field of Classification Search
USPC ........................... 604/385.22–385.3, 393–396
See application file for complete search history.

(56) References Cited

U.S. PATENT DOCUMENTS

| 4,857,067 | A | 8/1989 | Wood et al. |
| 5,242,436 | A | 9/1993 | Weil et al. |
| H1440 | H * | 5/1995 | New et al. ..................... 604/386 |

(Continued)

FOREIGN PATENT DOCUMENTS

| JP | 1168902 | 7/1989 |
| JP | 6508282 | 9/1994 |

(Continued)

OTHER PUBLICATIONS

International Search Report for PCT/JP2009/052646 mailed May 26, 2009.

(Continued)

*Primary Examiner* — Jackie Ho
*Assistant Examiner* — Kathryn E Ditmer
(74) *Attorney, Agent, or Firm* — Lowe Hauptman & Ham, LLP

(57) ABSTRACT

An absorptive article has an absorptive article body, a pair of side flaps, and a pair of waist flaps provided in the rear region so as to extend outward from the side flaps in the lateral direction of the absorptive article body. Each of the pair of waist flaps has formed thereon a waist stretchable region extended so as to reach that edge of the waist flap which is on the belly side. The waist stretchable regions are adapted such that the dimension of the waist stretchable region stretched at the end thereof on the belly side in the lateral direction of the absorptive article body is greater than the dimension of the waist stretchable region stretched at the end thereof on the rear side in the lateral direction of the absorptive article body.

8 Claims, 11 Drawing Sheets

(56) References Cited

U.S. PATENT DOCUMENTS

| | | |
|---|---|---|
| 5,947,948 A | 9/1999 | Roe et al. |
| 6,626,879 B1 * | 9/2003 | Ashton et al. ............ 604/385.03 |
| 6,692,476 B1 * | 2/2004 | Minato et al. ............ 604/385.27 |
| 2003/0109844 A1 * | 6/2003 | Gibbs ......................... 604/389 |
| 2003/0114828 A1 * | 6/2003 | Minato ....................... 604/389 |
| 2003/0120240 A1 | 6/2003 | Buell et al. |
| 2004/0127876 A1 * | 7/2004 | Stevens ..................... 604/385.3 |

FOREIGN PATENT DOCUMENTS

| | | | |
|---|---|---|---|
| JP | 9-509350 A | | 9/1997 |
| JP | 9509350 | | 9/1997 |
| JP | 2000-513642 A | | 10/2000 |
| JP | 2000513642 | | 10/2000 |
| JP | 2003180752 | | 7/2003 |
| JP | 2004290400 | | 10/2004 |
| JP | 2007-14802 A | | 1/2007 |
| JP | 2007014802 | | 1/2007 |
| WO | WO 2007149017 A1 * | | 12/2007 |
| WO | WO 2009082290 A1 * | | 7/2009 |

OTHER PUBLICATIONS

Official Action as issued on Jan. 29, 2013 in counterpart Japanese Patent Application No. 2009-554313.

Official Action as issued on Jan. 3, 2013 in counterpart EG Patent Application No. 1406/2010.

Official Action as issued on Jan. 28, 2013 in counterpart EA Patent Application No. 201001317.

Office Action issued Jun. 27, 2013 corresponds to EA patent application No. 201001317.

Office Action mailed Jul. 2, 2013 corresponds to Chinese patent application No. 200980100252.9.

* cited by examiner

ABSORPTIVE ARTICLE INCLUDING WAISTLINE STRETCHING REGIONS

RELATED APPLICATIONS

The present application is a national phase of PCT/JP2009/052646, filed Feb. 17, 2010, and claims priority from, Japanese Application Number 2008-037921, filed Feb. 19, 2008, the disclosure of which is hereby incorporated by reference herein in its entirety.

TECHNICAL FIELD

The present invention relates to an absorptive article, such as a diaper, providing a snug fit to a wearer.

BACKGROUND ART

Japanese Patent Application NO. 2004-290400P discloses a conventional diaper of this type. This diaper 100, as shown in FIG. 1, includes absorbent body 101 formed of: a liquid permeable top sheet 101a, a liquid impermeable back sheet (not shown), and an absorber 101c. Here, the absorber 101c is arranged between the top sheet 101a and the back sheet and is configured to absorb and hold fluid.

Here, in such diaper 100 a "dorsal side (rear side) Ba" and "ventral side (front side) Fr" are defined. The dorsal side Ba is located on the dorsal side of the wearer when the diaper 100 is put on, and the ventral side Fr is located on the ventral side of the wearer when the diaper 100 is put on.

In addition, the diaper 100 includes a dorsal side region S1, a crotch region S2, and a ventral side region S3, provided along a longitudinal direction L from the dorsal side Ba toward the ventral side Fr in this order.

The absorbent body 101 is configured such that the absorbent body 101 can cover the crotch portion of the wearer as a whole, from a dorsal side toward a ventral side.

On both sides of the absorbent body 101 in a width direction W, a side flap portion 110 is formed. Here, the top sheet 101a and the back sheet that are stretched so as to form the flap portion 110.

The dorsal side region S1 of each of the side flap portions 110 is provided with an elastic member 111 in a stretched state in the longitudinal direction.

On the dorsal region S1 of each side flap portion 110, pair of waist flap portions 120 is formed.

Each waist flap portion 120 has a long-and-thin belt like shape while being inclined (approximately 30°) with respect to a direction corresponding to a waistline direction of the wearer (the width direction W of the absorbent body 101).

A latch portion 130 is attached on an edge portion of each waist flap portion 120. The diaper 100 is put on the waistline of the wearer when the latch portion attached to one edge portion of one waist flap portion 120 is attached to the other waist flap portion 120.

An attach portion 140 is attached to the ventral region S3 of the absorber body 101.

When the attach portion 140 is attached from the outer side to the waist flap portion 120 being put on the waistline of the wearer, the absorber body 101 covers the portion around the crotch of the wearer.

According to this diaper 100, when being put on, the pair of waist flap portion 120 can be arranged by inclining to the dorsal side of the wearer with respect to the waistline direction of the wearer. Accordingly, the diaper 100 provides a snug fit to a body.

However, this diaper 100 needs to arrange the pair of waist flap portion 120 with inclining to the dorsal side of the wearer with respect to the waistline direction of the wearer (the width direction W of the absorber body 101). Accordingly, the manufacturing steps become complex and materials to be used for manufacturing such diaper 100 are increased.

SUMMARY

In this regard, an object of the present invention is to provide an absorptive article that can provide a snug fit to a body while its manufacturing process is not complex and does not require increased materials for manufacturing this absorptive article.

In the aspect of the invention is summarized as an absorptive article in which a dorsal side and a ventral side are defined and a dorsal side region, a crotch region, and a ventral side region are sequentially provided along with a longitudinal direction from the dorsal side toward the ventral side. The absorptive article includes: an absorbent body including a top sheet that is liquid permeable, a back sheet that is liquid impermeable, and an absorber located between the top sheet and the back sheet and being configured to absorb and hold fluid; a pair of side flap portions formed on both sides in a width direction of the absorbent body, in a vicinity of each side edge portions of the absorbent body, along with the longitudinal direction; and a pair of waist flap portions formed in the dorsal side region by extending from the pair of side flap portions toward outside in the width direction of the absorbent body. Each of the pair of side flap portions includes a waistline stretching region. A width size of a ventral side edge in the waistline stretching region becomes larger than a width size of a dorsal side edge in the waistline stretching region, when the absorptive article is stretched in a width direction. Each of the waistline stretching region reaches the ventral side edge of each of the pair of the side flap portions.

In the aspect of the invention, each of the waistline stretching region may not reach the dorsal side edge of each of the pair of waist flap portions.

In the first aspect of the invention, each of the waistline stretching region may reach the dorsal side edge of each of the pair of waist flap portions.

In the aspect of the invention, each of the waistline stretching region may be provided in a basal position in each of the pair of waist flap portions.

In the aspect of the invention, each a ventral side edge of each of the waistline stretching region may be stretched in a range of 1.1 to 3.0 times.

BRIEF DESCRIPTION OF THE DRAWINGS

FIGS. 9A and 9B show a second embodiment of the present invention and A is a plan view showing a state before being put on and B is a plan view showing a state after being put on.

FIGS. 10A and 10B show a third embodiment of the present invention and A is a plan view showing a state before being put on and B is a plan view showing a state after being put on.

DETAILED DESCRIPTION

Figure 1:
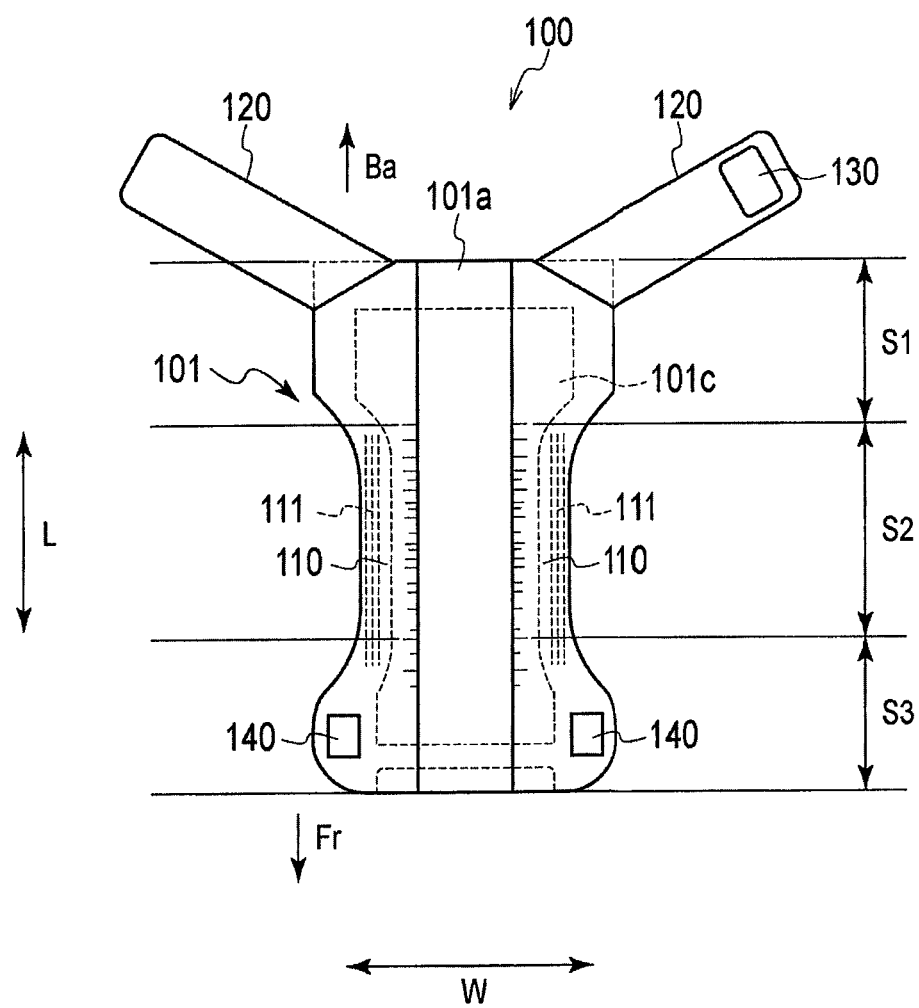
FIG. 1 is a plan view of a conventional diaper.

Embodiments of the present invention will be described below by referring to the drawings.

Figure 2:
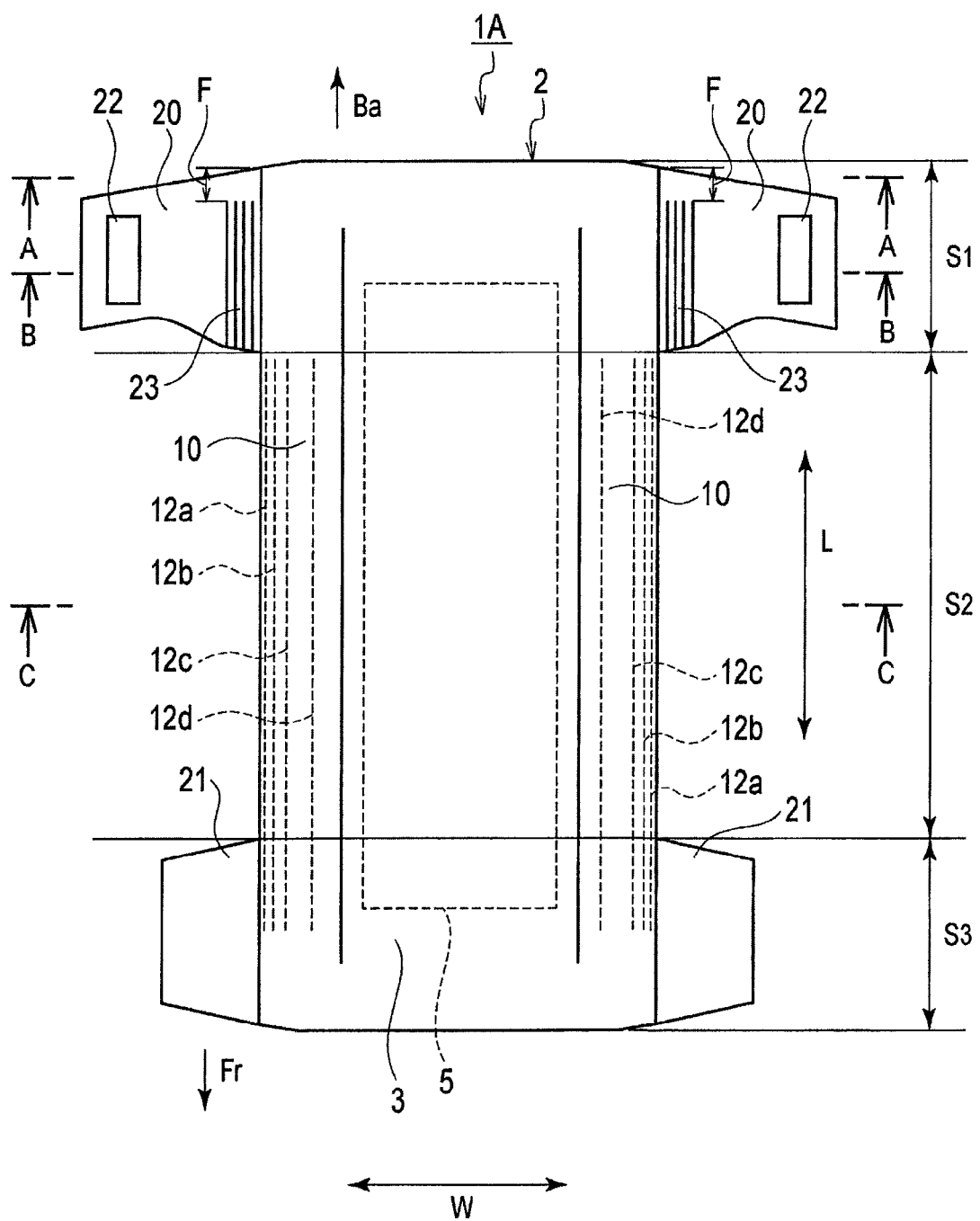
FIG. 2 shows a first embodiment of the present invention and is a plan view showing a diaper in a developed state.
Figure 3:
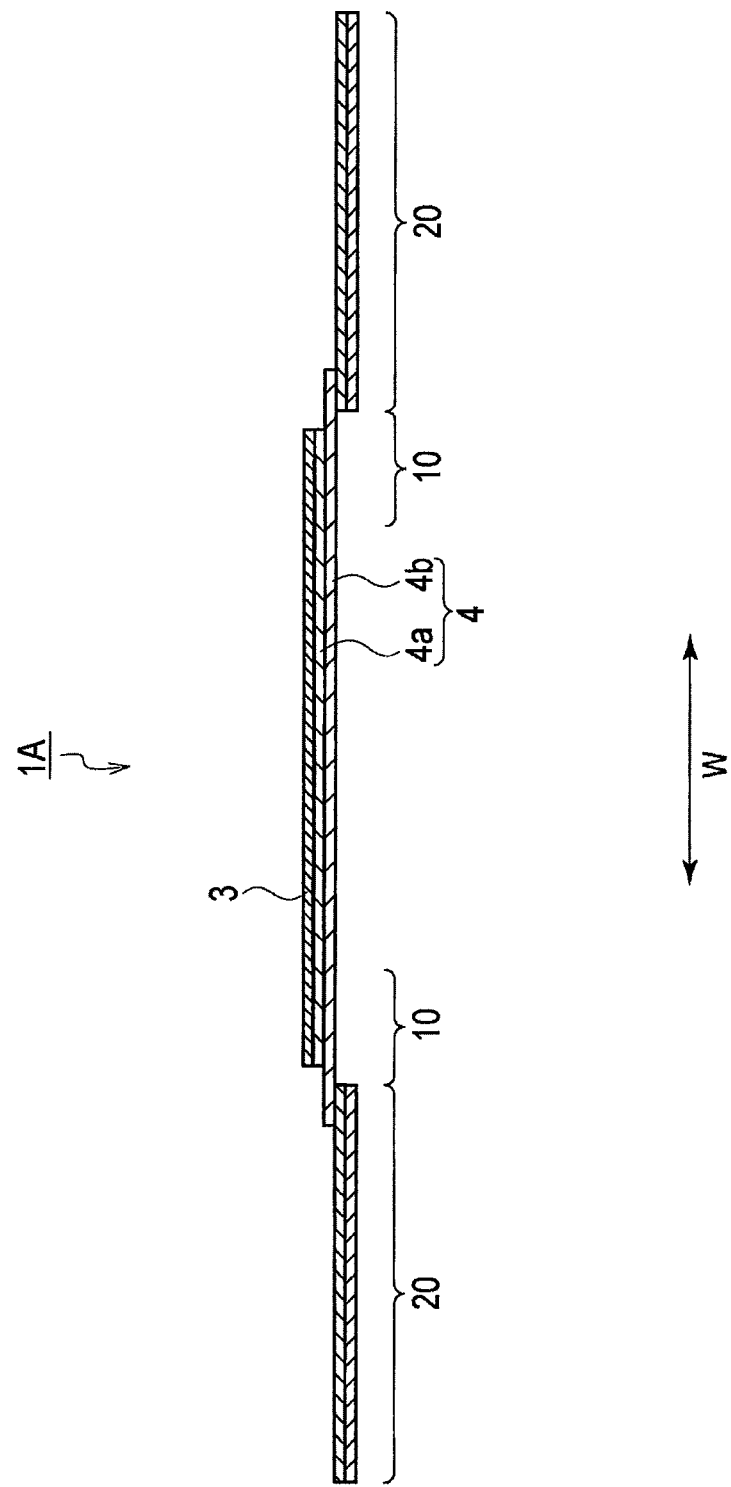
FIG. 3 shows the first embodiment of the present invention and is a cross-sectional view taken along A-A line in FIG. 2.
Figure 4:
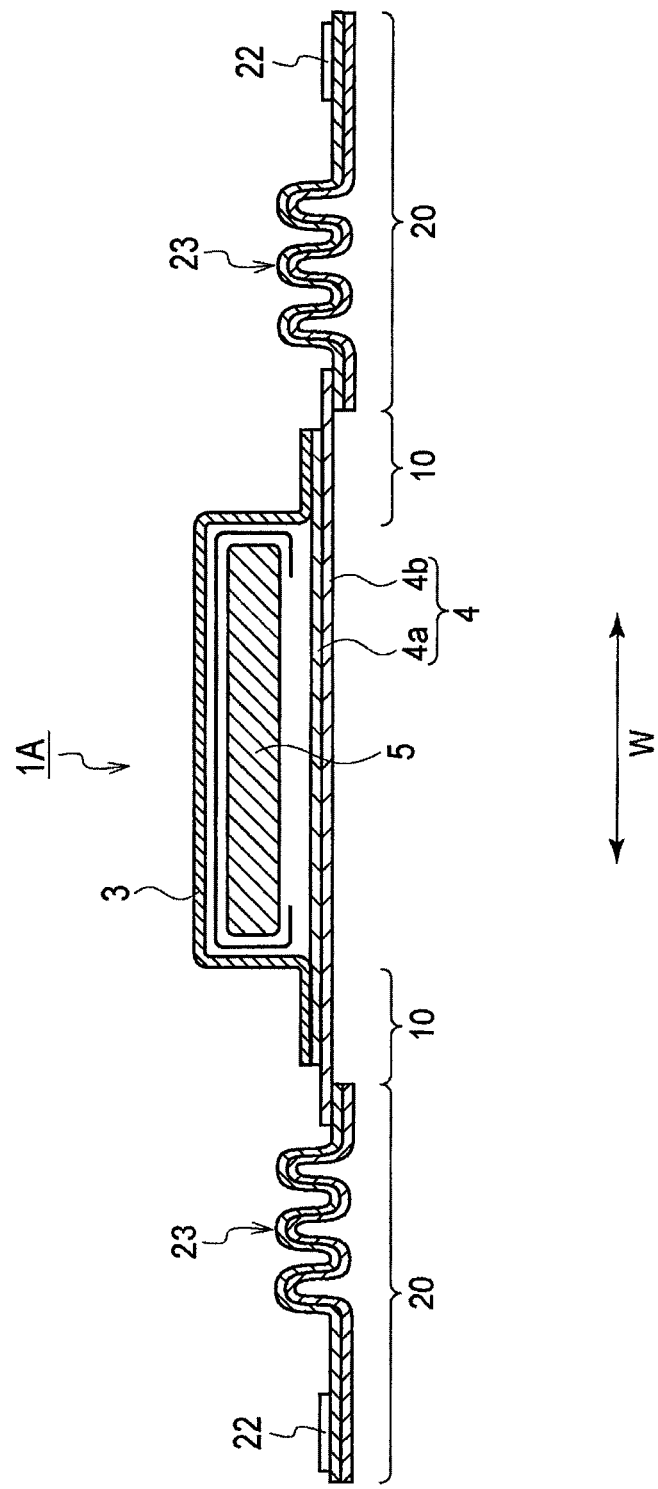
FIG. 4 shows the first embodiment of the present invention and is a cross-sectional view taken along B-B line in FIG. 2.
Figure 5:
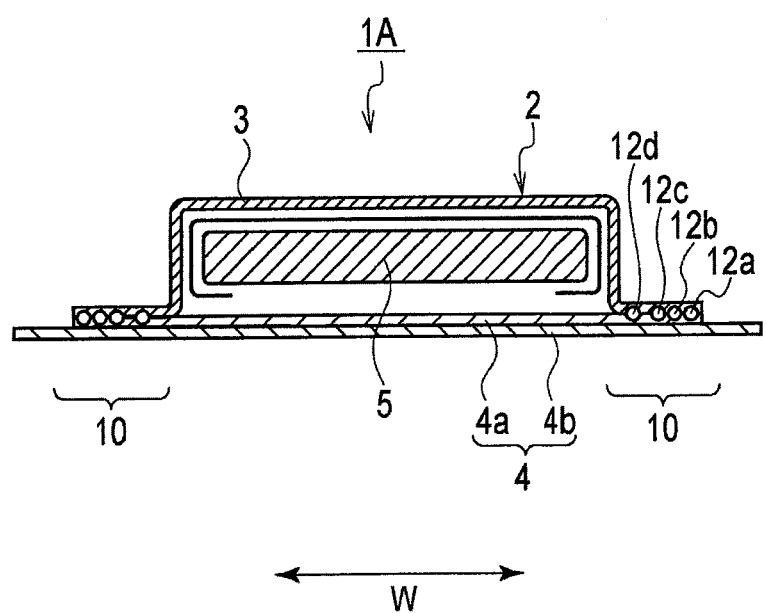
FIG. 5 shows the first embodiment of the present invention and is a cross-sectional view taken along C-C line in FIG. 2.
Figure 6:
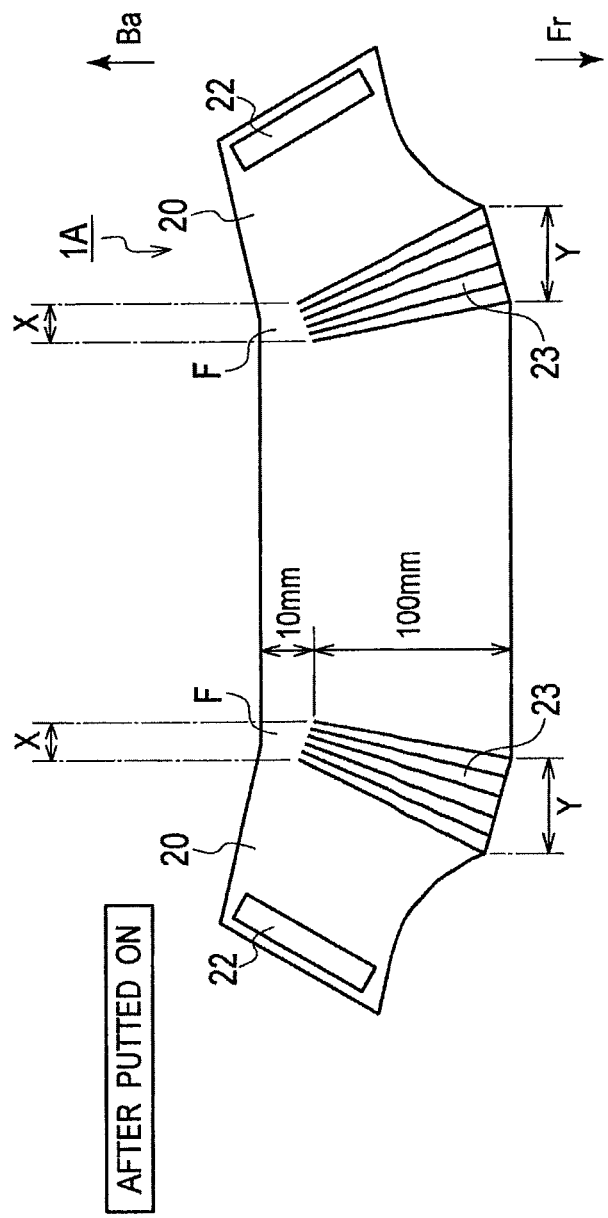
FIG. 6 shows the first embodiment of the present invention and is a plan view showing a put on state in a developed manner.
Figure 7:
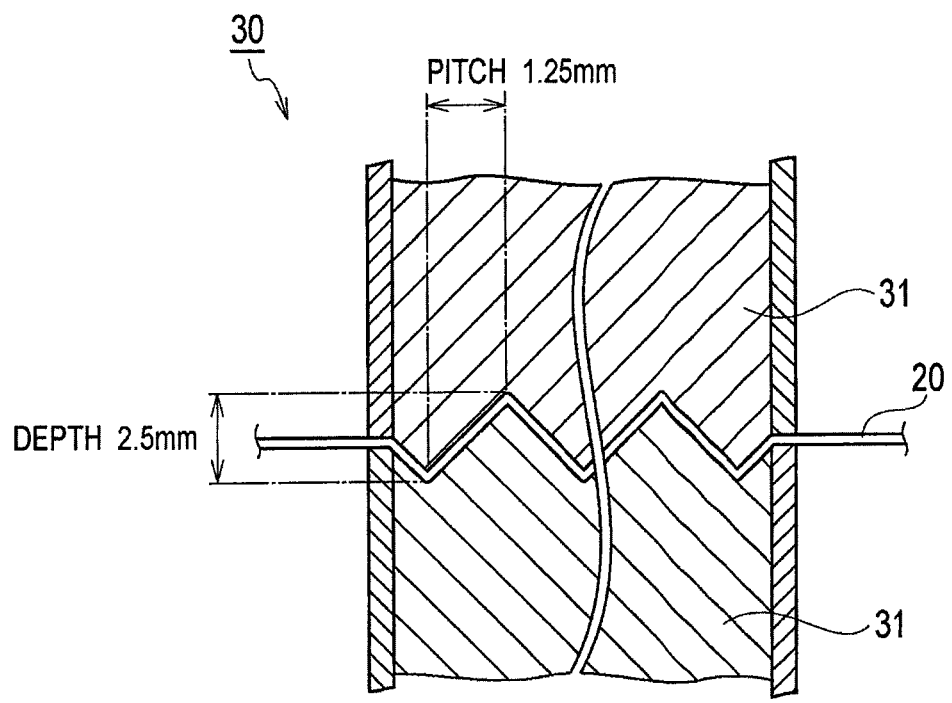
FIG. 7 shows the first embodiment of the present invention and is a cross-sectional view of a stretching apparatus.
Figure 8:
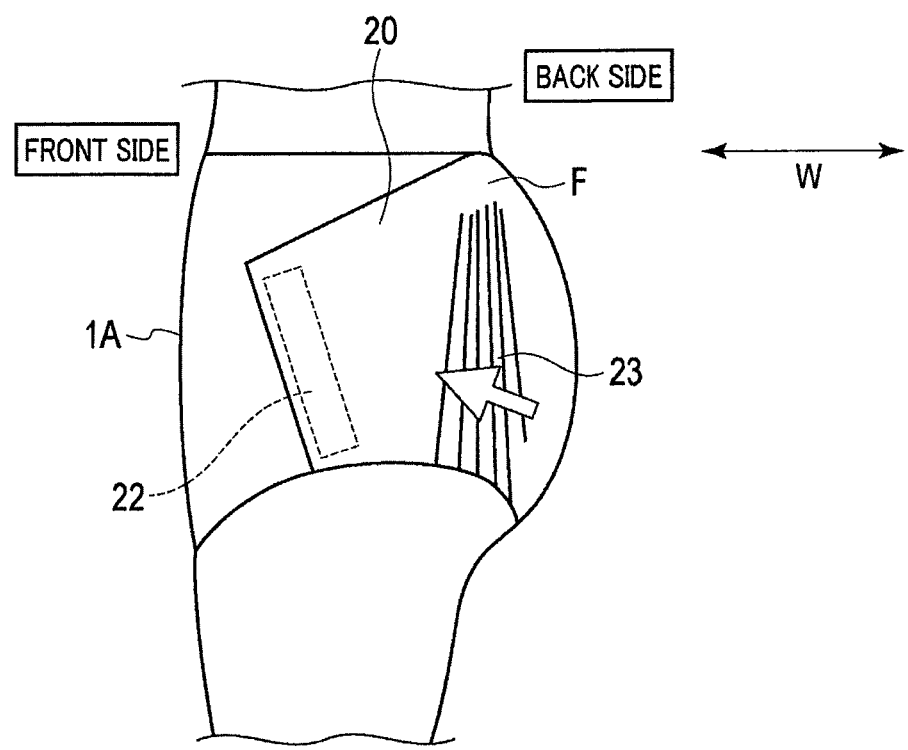
FIG. 8 shows the first embodiment of the present invention and is a side view of a wearing state.

FIG. 2 to FIG. 8 show a first embodiment of the present invention. FIG. 2 is a plan view of a diaper in a developed state. FIG. 3 is a cross-sectional view taken along the A-A line in FIG. 2. FIG. 4 is a cross-sectional view taken along the B-B line in FIG. 2. FIG. 5 is a cross-sectional view taken along the C-C line in FIG. 2. FIG. 6 is a cross-sectional view of an essential part of a stretching apparatus. FIG. 7 is a plan view of a waistline stretching region in a stretched state. FIG. 8 is a side view of a diaper being put on.

As shown in FIG. 2 to FIG. 6, a diaper 1A, which is an absorptive article, includes an absorbent body 2, a pair of side flap portions 10, which are provided on both sides of the absorbent body 2 in a width direction, a pair of dorsal side waist flap portions (waist flap portions) 20, and a pair of ventral side waist flap portions 21.

As shown in FIG. 2, a dorsal side Ba and the ventral side Fr are defined in the diaper 1A. Further, the diaper 1A includes the dorsal region S1, the crotch region S2, and the ventral side S3, along with a longitudinal direction L from the dorsal side toward the ventral side.

As shown in FIG. 2, the pair of side flap portions 10 is provided on both sides in a width direction W of the absorbent body 2, along with the longitudinal direction L.

Further, the pair of dorsal side waist flap portion 20 is provided in the dorsal side region S1 by extending from the pair of side flap portions 10 toward outside in the width direction W of the absorbent body 2.

Moreover, the pair of ventral side waist flap portion 21 in the ventral side region S by extending from the pair of side flap portions 10 toward outside in the width direction W of the absorbent body 2.

The absorbent body 2 includes at least a liquid permeable top sheet 3, a liquid impermeable back sheet 4, and an absorber 5. Here, the absorber 5 is located between the top sheet 3 and the back sheet 4, and absorbs and holds fluid. The absorbent body 2 includes a dorsal region S1, a crotch region S2, and a ventral region S3, and covers the dorsal side, crotch side, and ventral side, when the diaper 1A is put on.

The top sheet 3 is formed of a hydrophilic nonwoven, woven fabric, hydrophobic nonwoven having apertures, or the like.

The back sheet 4 is formed of a liquid impermeable nonwoven, liquid impermeable film, a sheet formed by bonding a hydrophilic nonwoven and a liquid impermeable film, or the like. In the present embodiment, a sheet in which a liquid impermeable film 4a and a liquid impermeable nonwoven 4b are bonded is used for the back sheet 4.

As the absorber 5, a laminated body in which absorbent pulp and high absorbent polymer are mixed is used.

The pair of side flap portions 10 is formed of the top sheet 3 and the back sheet 4, which are extended in the width direction W from both sides of the absorbent body 2.

An elastic member 12 is provided on at least the crotch region S2 of the pair of side flap portions 10 in a stretched state along the longitudinal direction L of the side flap portion 10.

As the elastic member 12, an elastic member in which four polyurethane-based elastic yarns (470 dtex) 12a-12d are stretched with the magnification of 2.2 times is used.

The pair of dorsal side waist flap portions 20 and the pair of ventral side waist flap portions 21 extend in a direction corresponding to a waistline direction (the width direction W of the absorbent body 2).

That is, the pair of dorsal side waist flap portions 20 is formed so as to extend outwardly in the width direction W from the dorsal region S1 of the pair of side flap portions 10. The pair of ventral side waist flap portions 21 is formed so as to extend outwardly in the width direction W form the ventral region S3 of the pair of side flap portions 10.

In this regard, the dorsal side waist flap portions 20 and the ventral side waist flap portions 21 are formed of a liquid impermeable nonwoven.

Among the dorsal side waist flap portions 20 and the ventral side waist flap portions 21, the dorsal side waist flap portion 20 is particularly formed of a nonwoven that is liquid impermeable and can thermally expand. The dorsal side waist flap portions 20 in the present embodiment are formed by bonding together two sheet materials with SMS of 13 g/m$^2$ (see, FIG. 4).

On tip end sides of the pair of dorsal side waist flap portions 20, latch portions 22 are provided.

The latch portion 22 attaches and is locked on the ventral side waist flap portion 21. As the latch portion 22, a hook-and-loop fastener to lock with mechanical locking strength or an adhesive tape to lock with adhesion can be used.

When a hook-and-loop fastener is used as the latch portion 22, a sheet material having at least a surface made of a nonwoven is used as the ventral side waist flap portion 21.

A waistline stretching region 23 is formed on each of the pair of dorsal side waist flap portions 20.

Each of the waistline stretching region 23 is provided in a vicinity of the side flap portion 10, that is, in a basal portion.

Moreover, each of the waistline stretching region 23 is formed while extending outwardly from the ventral side Fr end along with the absorbent body 2 in the longitudinal direction.

The extended edge of the waistline stretching region 23 comes up to the verge of the dorsal side edge of the dorsal side waist flap portion 20, but does not reach the dorsal side edge of the dorsal side waist flap portion 20. Accordingly, in the dorsal side edge of the dorsal side waist flap portion 20, a non-stretching region F exists.

In the present embodiment, the longitudinal size of the waistline stretching region 23 is set to be 100 mm and the longitudinal size of the non-stretching region F is set to be 10 mm.

The waistline stretching region 23 is a region in which a basis weight is lowered than those of other regions by the stretching process.

As shown in FIG. 4, the waistline stretching region 23 formed by the stretching process has a structure in which a dense portion (reference numeral is not given) whose stretched amount is small and a sparse portion (reference numeral is not given) whose stretched amount is large are alternately provided in the width direction W of the side flap portion 10.

The stretching process is performed so that the size of the edge portion of the ventral side Fr in the waistline stretching region 23 when stretched in the width direction W is to be larger than the size of the edge portion of the dorsal side Ba in the waistline stretching region 23 in the width direction W.

By performing such a stretching process, a stretched amount on the dorsal side Ba on the dorsal side waist flap portion 20 can be small, whereas a stretched amount on the crotch side can be large, when the diaper 1A is put on. Accordingly, the diaper 1A can fit a crotch portion of a wearer.

The waistline stretching region 23 will be described in detail by referring to FIG. 6. In FIG. 6, X indicates a width size of the width direction W of the waistline stretching region 23 before being stretched (i.e. the stretched amount), and Y is a width size of the width direction W of the waistline stretching region 23 after being stretched (i.e. the stretched amount).

As described above, setting is made to be X<Y. It is preferable that Y is set to have a difference of 0.5 to 10 cm in relation to X.

If the width size difference made by the stretch is less than 0.5 cm, a gap between circumferential width sizes of waist and hip cannot be covered by the stretched width size of the waistline stretching region 23, because the difference between the width sizes before and after the stretch is too small for a child whose difference between the circumferential width sizes of waist and hip is 1 cm at the smallest.

As a result, a gap is generated in the waist portion, and fitting property is deteriorated, which causes a misalignment of the diaper or excrement leakage while being put on.

On the other hand, when the size difference by the stretch exceeds 10 cm, a size difference between the stretched portion and the non-stretched portion becomes too large for an adult whose difference between the circumferential width sizes of waist and hip is approximately 20 cm at maximum. Accordingly, a gap is generated in the hip portion that is stretched by the stretch, and the fitting property is deteriorated, which results in the misalignment of the diaper or the excrement leakage while being put on.

FIG. 7 shows a stretching apparatus 30 for performing the stretching process. The stretching apparatus 30 has a pair of stretching blade line portions 31 which are opposite to each other and can be intermeshed to each other.

Each stretching blade line portion 31 has a blade depth of 2 mm, a pitch between the pair of blades of 1.25 mm, and the number of the blades 17.

The dorsal side waist flap portion 20 is heated up to a temperature near a melting point, and thereafter is inserted between the stretching blade line portions 31. Then, the stretching process is performed by setting the temperature of the stretching blade line portions 31 to be 100° C.

By heating the stretching blade line portions 31, the material of the dorsal side waist flap portion 20 comes near to the melting point and becomes easily stretched. Accordingly, the damage of the material caused by the stretching process can be reduced.

In addition, if heating to the dorsal side waist flap portion 20 from the blades to the material is insufficient as the process rate is increased, preheating may be performed in front of the stretching blade line portions 31.

With this stretch by such a stretching apparatus 30, a dense portion in which a stretched amount is small and a sparse portion in which a stretched amount is large are alternately provided in the width direction W of the side flap portion 10 in the dorsal side waist flap portion 20.

FIG. 8 shows a state where the diaper 1A with the above-described configuration is being put on. The diaper 1A is in the wearing state when the latch portion 22 on the dorsal side waist flap portion 20 is locked on the front surface of the ventral side waist flap portion 21.

When the wearer puts on the diaper 1A, the circumference of each side flap portion 10 fits around legs of the wearer with the contraction of each of the elastic members 12a to 12d.

In the dorsal side waist flap portion 20, the non-stretching region F does not stretch in the width direction W of the absorber body 101, but the waistline stretching region 23 stretches in the width direction W of the absorber body 101. Accordingly, a size difference between X and Y is caused as described above.

As a result, the diaper can preferably fit not only around the waist but also around the hip that is larger than the waist.

In this regard, it is preferable that the edge of the ventral side Fr in the waistline stretching region 23 on the dorsal side waist flap portion 20 should be stretched in a range of 1.1 to 3.0 times, on the assumption that the size is large enough for covering the hip portion and that the material damage is not caused.

If the stretched amount is less than 1.1 times, the waistline size of the dorsal side waist flap portion 21 may be too small to sufficiently cover the hip portion. If the stretched amount is more than 3.0 times, the damage of the material, such as a torn or a hole, is likely to occur due to the severe damage from the stretch.

In addition, it is further preferable that the edge on the ventral side Fr of the waistline stretching region 23 should be stretched in a range of 1.2 to 2.0 times, considering that a fitting property to the hip portion and a prevention of a damage on the material.

In addition, each dorsal waist flap 20 can be provided in the direction corresponding to the waistline direction of the wearer (the width direction W of the absorbent body 2). Accordingly, increased materials are not required and the manufacturing process is not complex.

In this embodiment, the dorsal side waist flap portion 20 stretches only in the waistline stretching region 23 and the entire portion does not stretch. Accordingly, the waistline size before being put on is maintained even during the diaper 1A is put on, and thus the diaper 1A is not displaced.

In this embodiment, in the longitudinal direction L of the dorsal side waist flap portion 20, a portion other than the waistline stretching region 23 (non-stretching region F) exists. Accordingly, the deterioration in strength of the dorsal side waist flap portion 21 can be prevented as much as possible.

In this embodiment, the waistline stretching region 23 is provided in the basal position of the dorsal side waist flap portion 20 (near the side flap portion 10). Accordingly, a displacement amount in relation to the inclination at the tip end in the width direction W of each of the dorsal side waist flap portions 20 can be greatly obtained. Thus, a desired displacement amount can be obtained while keeping the width size of the waistline stretching region 23 small.

Note that, the width size in the longitudinal direction L of the dorsal side waist flap portion 20 is determined by the physique of the wearer or the design of the entire diaper, and is not particularly limited. However, it is preferable that an angle formed by an imaginary line in the width direction W of the diaper 1A, which is made by the stretch of the dorsal side waist flap portion 20 when the diaper is put on, is 0° to 30°.

If this angle is less than 0°, a length around the waist becomes longer than a length around the hip. Accordingly, a fitting property cannot be obtained. If this angle is more than 30°, the tension of the dorsal side waist flap portion 20 is hardly applied in the direction around the waist. Accordingly, the fitting property is deteriorated, which is not preferable.

It should be noted that, in this embodiment, the dorsal side waist flap portion 20 and the ventral side waist flap portion 21 are configured of a member independent of that of the side flap portion 10. However, they may be formed as a same member. With such a configuration, the manufacturing the diaper can be simplified.

Figure 9:
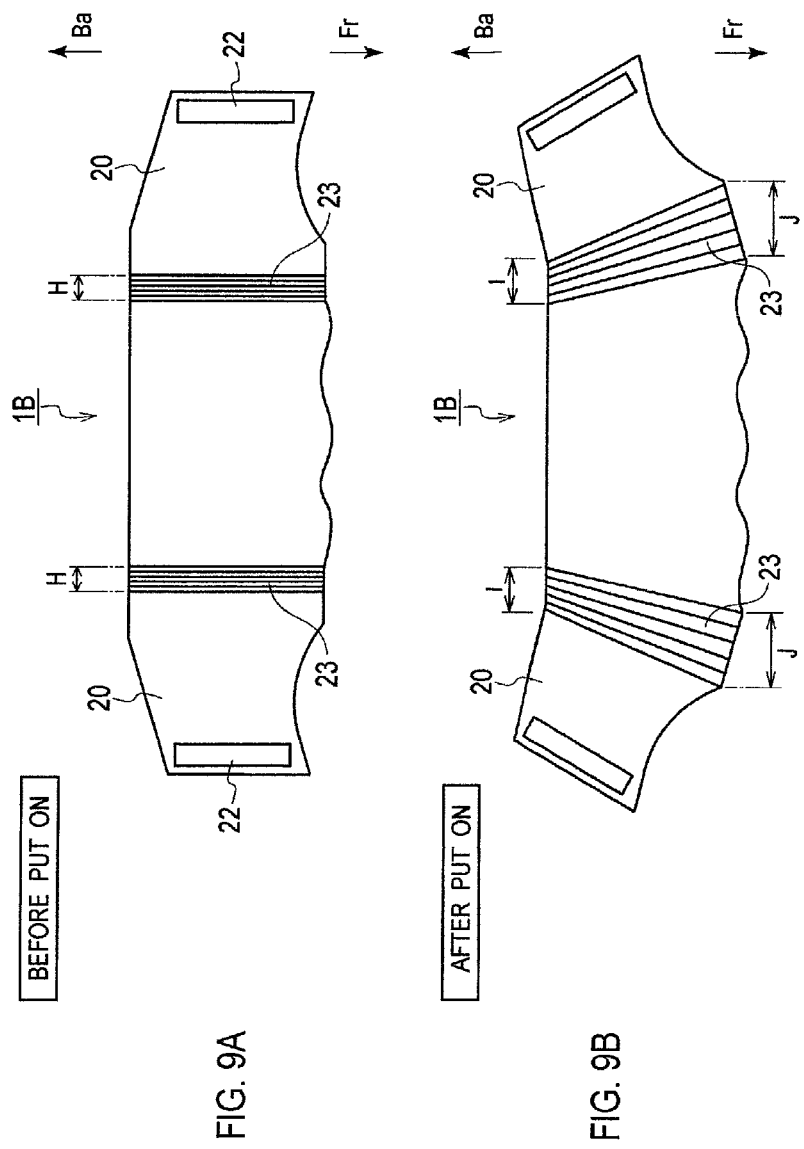

FIG. 9 is a plan view of a diaper 1B according to a second embodiment of the present invention, and A shows a state before being put on and B shows a state after being put on.

A diaper 1B according to the second embodiment has a waistline stretching region 23 formed up to both edges in the longitudinal direction L of each dorsal side waist flap portion 20, unlike the first embodiment.

That is, the waistline stretching region 23 is formed across the entire length of the dorsal side waist flap portion 20.

In addition, the waistline stretching region 23 has the same width size in which a stretching process is performed across the entire length of the dorsal side waist flap portion 20. However, in the waistline stretching region 23, a stretched amount per unit width size is different.

Thus, the width size of the waistline stretching region 23 in the ventral side Fr is configured to be larger than the width size of the waistline stretching region 23 in the dorsal side Ba, when the diaper 1B is stretched (during being put on).

That is, as shown in FIG. 9A, the width size of the waistline stretching region 23 before being put on is a size H, but, as shown in FIG. 9B, the stretching region 23 on the dorsal side after being put on becomes a size I (H<I). Further, the ventral stretching region 23 on the ventral side Fr after being put on becomes a size J (H<J, and I<J).

By setting the stretched amounts in the aforementioned manner, a fitting property similar to that of the first embodiment can be secured.

The stretching process in manufacturing the diaper 1B of this embodiment can be performed by changing a depth of a blade of a stretching blade line portion 31 on the dorsal side Ba and the ventral side Fr.

Other configurations are the same as those of the first embodiment, and the duplicated description thereof will be omitted. Also, the same reference numerals are given to denote same portions in the figures for clarification.

In this embodiment, even when the stretching width in the longitudinal direction L of the waistline stretching region 23 is the same, the edge portion of the waistline stretching region 23 is restrained by a portion which is not the waistline stretching region 23. Accordingly, the stretched amount at the edge portion is small, and the stretched amount increases as it recedes from the edge portion.

Thus, the waistline stretching region 23 can be obtained without wasting a material when an inclined shape is formed.

Figure 10:
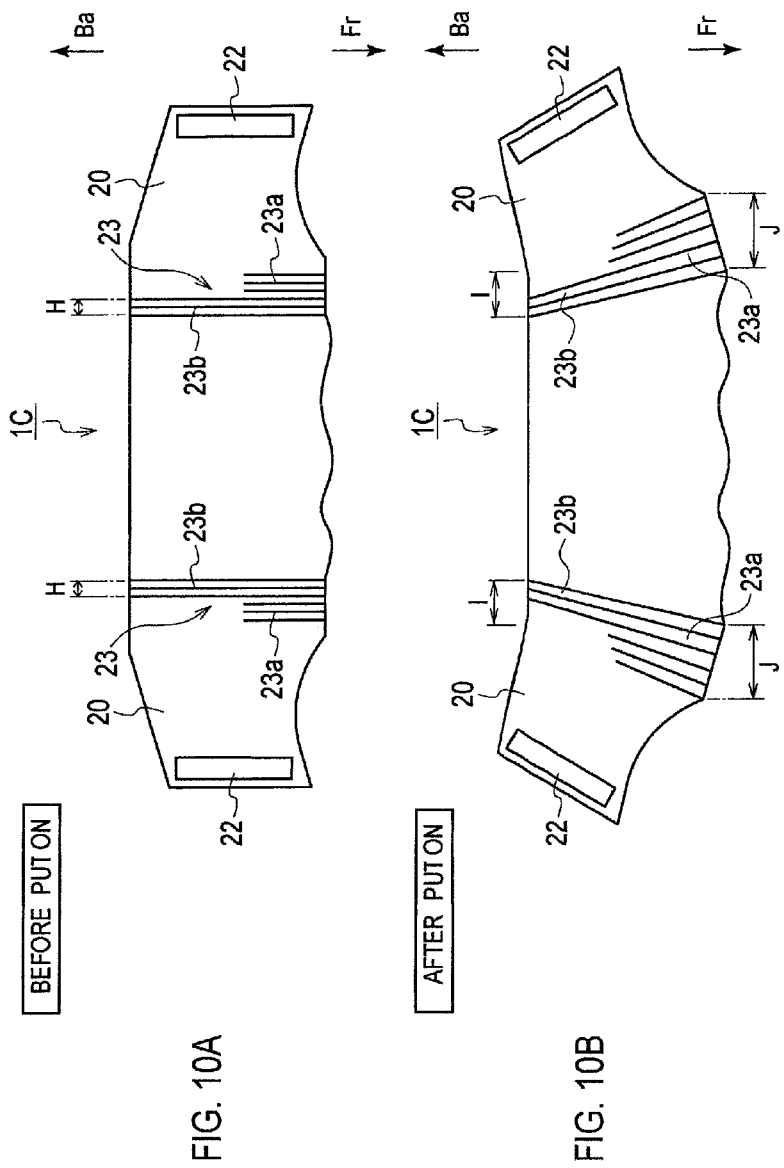

FIG. 10 is a plan view of a diaper 1C according to a third embodiment of the present invention. FIG. 10A shows a state of the diaper 1C before being put on, and FIG. 10B shows a state of the diaper 1C after being put on.

The diaper 1C according to the third embodiment has, similar to the second embodiment, a waistline stretching region 23 formed across a dorsal side waist flap portion 20 on its entire length.

In this third embodiment, the waistline stretching region 23 has different width sizes in a region having the stretching process performed. Here, the width side of the waistline stretching region 23 in the ventral side Fr is set to be large, whereas the width size of the waistline stretching region 23 in the dorsal side Ba is set to be small.

Thus, the width size of the ventral side Fr in the waistline stretching region 23 becomes larger than the width size of the dorsal side Ba in the waistline stretching region 23 when being stretched (during the diaper 1C is put on).

In other words, as shown in FIG. 10A, the width size of the waistline stretching region 23 before being put on is a width size H, but, as shown in FIG. 10B, the width size of the dorsal side stretching region 23b after being put on becomes a width size I (H<I). Further, the width size of the waistline stretching region 23a after being put on becomes a width size J (H<J, and I<J).

By setting the stretched amounts having such relationships, a fitting property similar to that of the first embodiment can be secured.

Other configurations are same as those of the second embodiment, and the duplicated description thereof will be omitted. Also, same reference numerals are given to denote same portions in the figures for clarification.

In the present embodiment, a displacement amount in relation to the inclination at a tip end side in the width direction W of each dorsal side waist flap portions 20 can be largely obtained. Accordingly, the width size or the stretching extent of the waistline stretching region 23 can be minimized as less as possible and a desired displacement amount can be obtained.

Figure 11:
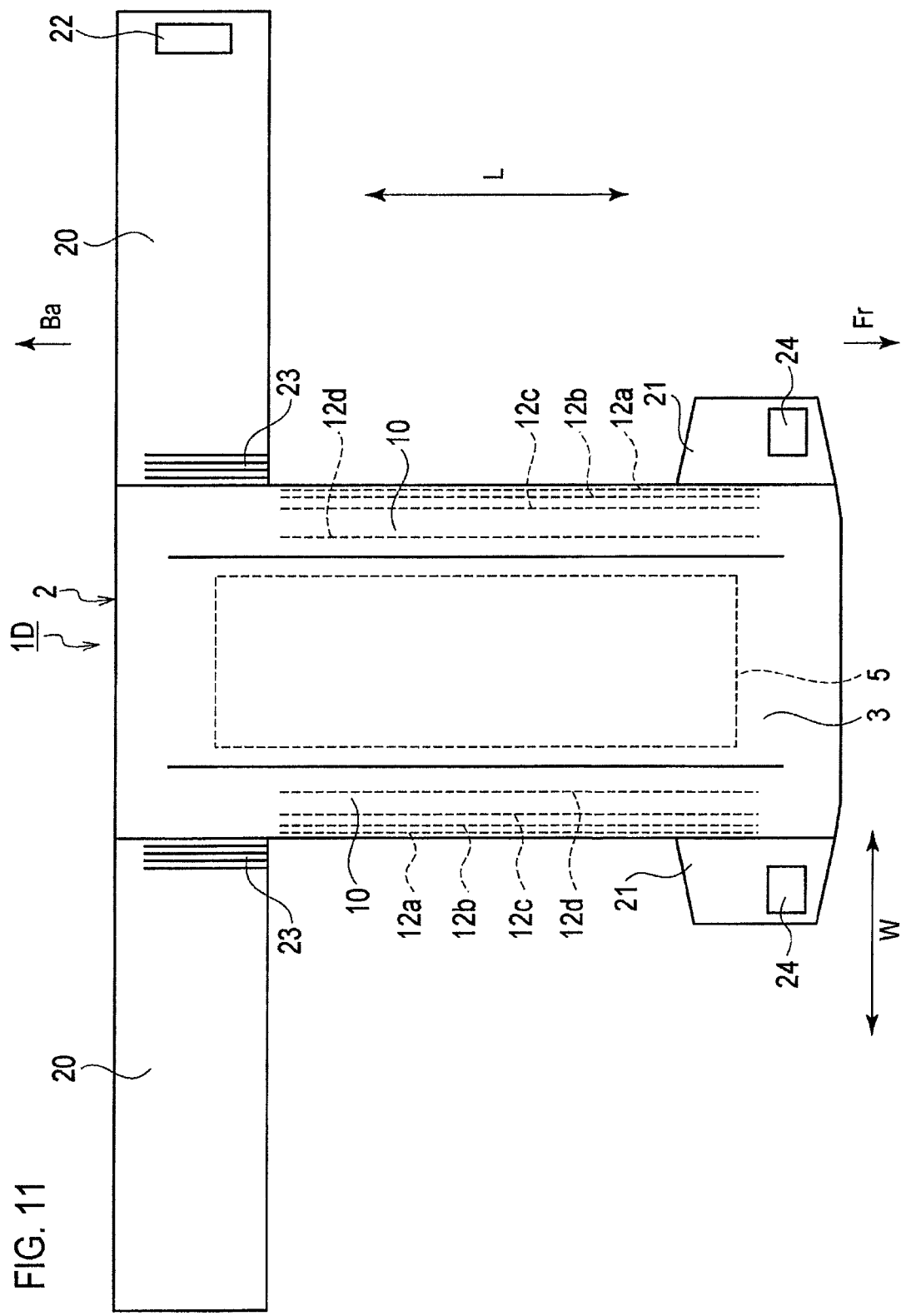
FIG. 11 shows a fourth embodiment of the present invention and is a plan view showing a developed state of a diaper.

FIG. 11 is a plan view of a diaper 1D according to a fourth embodiment of the present invention.

A diaper 1D according to the fourth embodiment is a belt type. In the diaper 1D, a pair of dorsal side waistline flap portion 20 is provided while extending outwardly in a direction crossing the longitudinal direction L of the absorbent body 2.

A latch portion 22 is provided on one of the dorsal side waist flap portions 20.

A pair of ventral side waist flap portions 21 is also provided in a direction crossing the longitudinal direction L of the absorber body 2, and a latch portion 24 is provided on the each of the pair of the ventral side waist flap portions 21 so that the diaper 1D can be put on.

In this embodiment, since the waistline stretched portion 23 is provided on the outside in the width direction W of each side flap portion 10, the fitting property can be improved.

As described above, according to the absorptive article of the present invention, a pair of waist flap 20 can be provided in the direction corresponding to the waistline direction of the wearer (the width direction W of the absorbent body 2) when the article is manufactured. When being put on, the pair of waist flap 20 can be arranged in the direction inclining to the dorsal side of the wearer with respect to the waistline direction of the wearer in each waistline stretching region 23.

Therefore, according to the present invention, there can be provided an absorptive article that can provide a snug fit to a body while its manufacturing process is not complex and does not require increased materials for manufacturing this absorptive article.

The invention claimed is:

1. An absorptive article having a dorsal side and a ventral side, the absorptive article comprising:
    a dorsal side region, a crotch region, and a ventral side region sequentially provided along a longitudinal direction from the dorsal side toward the ventral side;
    an absorbent body including a liquid permeable top sheet, a liquid impermeable back sheet, and an absorber located between the top sheet and the back sheet for absorbing fluid, said absorbent body further including a pair of side edge portions extending in the longitudinal direction;
    a pair of side flap portions formed on both sides of the absorbent body in a width direction transverse to the longitudinal direction, in a vicinity of the corresponding side edge portions of the absorbent body; and a pair of waist flap portions formed in the dorsal side region and outwardly extending from the pair of side flap portions in the width direction, respectively, wherein each of the pair of waist flap portions includes
- a waistline stretching region; and
- a ventral side edge and a dorsal side edge opposite to the ventral side edge in the longitudinal direction, the waist flap portions are stretchable in the width direction only in the waistline stretching regions, regions of the waist flap portions outside the waistline stretching regions are not stretchable in the width direction, a width of the ventral side edge in the waistline stretching region is larger than a width of the dorsal side edge in the waistline stretching region, when the absorptive article is stretched in the width direction, each of the waistline stretching regions extends to the ventral side edge of the corresponding waist flap portion, and each of the waistline stretching regions does not extend to the dorsal side edge of the corresponding waist flap portion.

2. The absorptive article according to claim 1, wherein each of the waistline stretching regions is provided in a basal position in the corresponding one of the pair of waist flap portions.

3. The absorptive article according to claim 1, wherein the ventral side edge of each of the waistline stretching regions is stretchable in the width direction in a range of 1.1 to 3.0 times of an original length of the ventral side edge.

4. The absorptive article according to claim 1, wherein the ventral side region is free of waist stretching regions.

5. The absorptive article according to claim 1, wherein an entirety of each of the waistline stretching regions is outboard of the corresponding side edge portion of the absorbent body in the width direction.

6. The absorptive article according to claim 1, wherein the waist flap portions are directly attached to outer surfaces of the side flap portions on a non-skin facing side of the absorptive article.

7. The absorptive article according to claim 1, wherein the waist flap portions are defined by separate pieces, and each of the waist flap portions is separately and directly attached to an outer surface of the corresponding side flap portion on a non-skin facing side of the absorptive article.

8. The absorptive article according to claim 7, wherein each of the waist flap portions includes a side edge directly attached to the outer surface of the corresponding side flap portion, and the side edges of the waist flap portions are spaced away from each other in the width direction.

* * * * *